(12) United States Patent
Gilmour

(10) Patent No.: US 6,837,863 B2
(45) Date of Patent: Jan. 4, 2005

(54) BODY JOINT LINER

(75) Inventor: Robert Farrer Gilmour, Auckland (NZ)

(73) Assignee: Bodyworks Inc., Vista, CA (US)

( * ) Notice: Subject to any disclaimer, the term of this patent is extended or adjusted under 35 U.S.C. 154(b) by 0 days.

(21) Appl. No.: 10/153,606

(22) Filed: May 24, 2002

(65) Prior Publication Data

US 2003/0014000 A1 Jan. 16, 2003

(30) Foreign Application Priority Data

May 25, 2001 (NZ) .............................................. 511913

(51) Int. Cl.[7] .............................................. A61F 5/00
(52) U.S. Cl. ....................... 602/27; 128/882; 601/138; 36/43
(58) Field of Search ................... 128/882; 36/43, 36/47, 44; 601/138, 134; 602/27, 65, 66, 26, 23, 5

(56) References Cited

U.S. PATENT DOCUMENTS

| | | | | |
|---|---|---|---|---|
| 2,300,681 A | * | 11/1942 | Margolin | 36/3 B |
| 3,722,113 A | * | 3/1973 | Birkenstock | 36/11.5 |
| 3,856,008 A | * | 12/1974 | Fowler et al. | 602/62 |
| 3,888,242 A | * | 6/1975 | Harris et al. | 601/152 |
| 4,075,772 A | * | 2/1978 | Sicurella | 36/43 |
| 4,156,425 A | * | 5/1979 | Arkans | 601/152 |
| 4,281,467 A | * | 8/1981 | Anderie | 36/32 R |
| 4,345,387 A | * | 8/1982 | Daswick | 36/43 |
| 4,402,145 A | * | 9/1983 | Dassler | 36/32 R |
| 4,521,979 A | * | 6/1985 | Blaser | 36/29 |
| 4,628,945 A | * | 12/1986 | Johnson, Jr. | 602/27 |
| 4,674,203 A | * | 6/1987 | Goller | 36/44 |
| 4,685,224 A | * | 8/1987 | Anger | 36/43 |
| 4,756,096 A | * | 7/1988 | Meyer | 36/44 |
| 4,896,441 A | * | 1/1990 | Galasso | 36/43 |
| 4,897,937 A | * | 2/1990 | Misevich et al. | 36/43 |
| 4,934,071 A | * | 6/1990 | Virgini | 36/29 |
| 5,035,068 A | * | 7/1991 | Biasi | 36/3 R |
| 5,074,285 A | * | 12/1991 | Wright | 601/15 |
| 5,301,370 A | * | 4/1994 | Henson | 2/22 |
| 5,366,439 A | * | 11/1994 | Peters | 602/27 |
| 5,403,265 A | * | 4/1995 | Berguer et al. | 601/151 |
| D373,013 S | * | 8/1996 | Rosetta | D2/961 |
| 5,625,965 A | * | 5/1997 | Blissett et al. | 36/43 |
| 5,716,335 A | * | 2/1998 | Iglesias et al. | 602/27 |
| D404,548 S | * | 1/1999 | McDonald | D2/956 |
| 5,860,229 A | * | 1/1999 | Morgenstern | 36/141 |
| 5,876,364 A | * | 3/1999 | Herbst | 602/27 |
| 5,896,680 A | * | 4/1999 | Kim et al. | 36/28 |
| 5,916,183 A | * | 6/1999 | Reid | 601/134 |
| 5,971,946 A | * | 10/1999 | Quinn et al. | 602/27 |
| 5,992,055 A | * | 11/1999 | Connor | 36/43 |
| 6,142,961 A | * | 11/2000 | Salley | 601/1 |
| 6,189,172 B1 | * | 2/2001 | Baek | 12/142 P |
| 6,214,027 B1 | * | 4/2001 | Brossard | 606/201 |
| 6,254,554 B1 | * | 7/2001 | Turtzo | 601/134 |
| 6,425,194 B1 | * | 7/2002 | Brie | 36/43 |
| 6,488,643 B1 | * | 12/2002 | Tumey et al. | 602/13 |
| 2002/0042585 A1 | * | 4/2002 | Kloecker | 602/13 |

* cited by examiner

Primary Examiner—Nicholas D. Lucchesi
Assistant Examiner—Huong Q. Pham
(74) Attorney, Agent, or Firm—Young & Thompson

(57) ABSTRACT

A body joint liner including at least one divergent channel such that when in use on a persons body, tissue fluid flow is encouraged. A body joint liner including a first pressure gradient for tissue fluid flow when in use on a persons body. A body joint liner including a pressure gradient including a pattern of projections with a spacing that increases along the length of the liner.

16 Claims, 1 Drawing Sheet

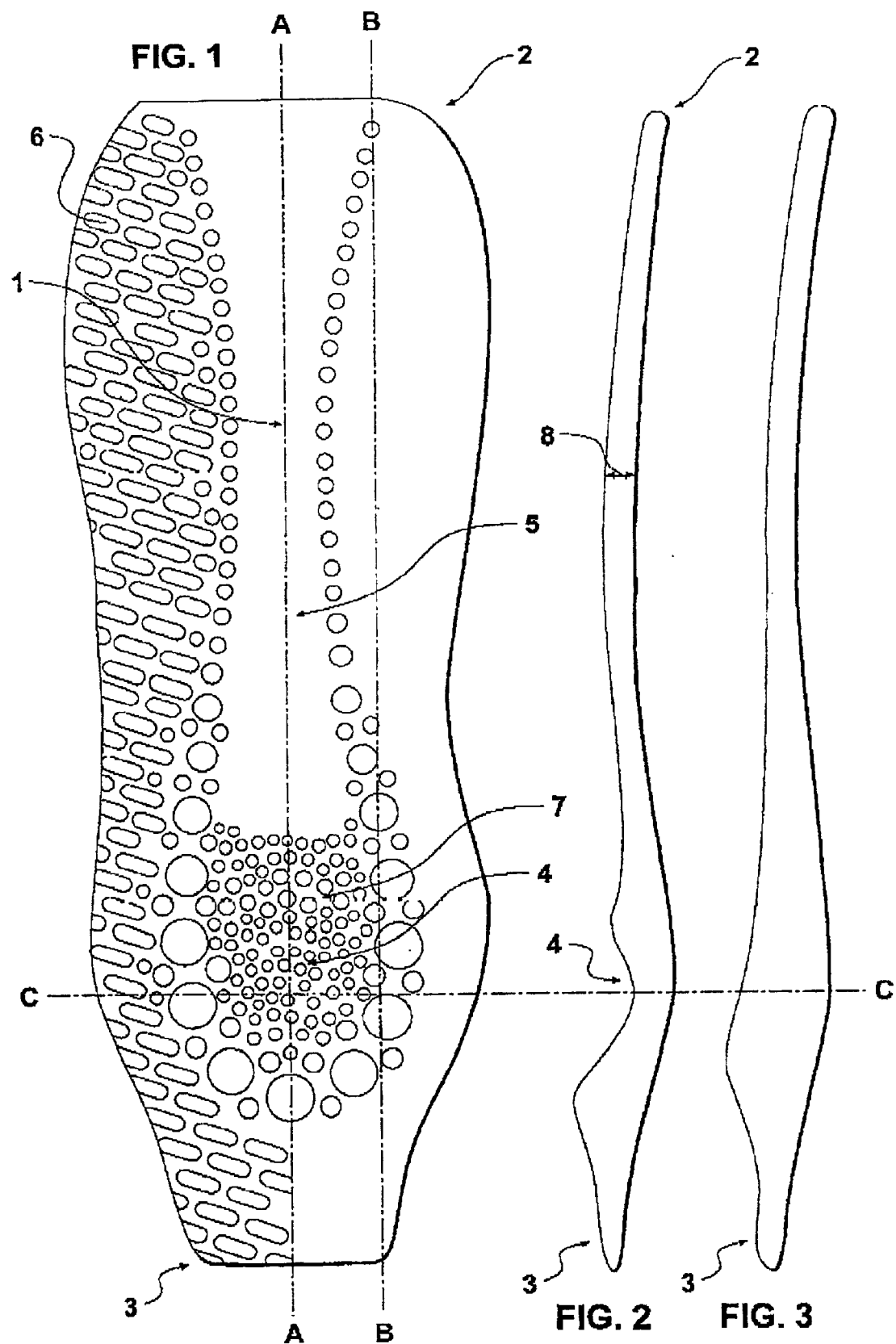

BODY JOINT LINER

FIELD OF THE INVENTION

This invention relates to a body joint liner for an ankle brace for human use.

BACKGROUND OF THE INVENTION

There are a variety of known ankle brace designs of what are frequently called clamshell ankle braces. These braces consist of a pair of shells and body joint liners, that attach to either side of the ankle joint. They are fitted following common soft tissue ankle injuries, such as what is known as an inversion injury which is accompanied by oedema (swollen tissue). Following the injury regaining ones health and fitness as quickly as possible is very important. A factor influencing the healing process, is the ease with which tissue fluid drains from the injury site. Also the muscles surrounding the body joint may be damaged which may effect a person's balance.

Existing braces provide a moulded foam liner with a straight channel running up the middle of the liner. This channel provides an area of lesser pressure and so encourages drainage of tissue fluid following the common inversion injury. Some examples of prior art are U.S. Pat. Nos. 4,844,094, 5,389,065 and 5,630,792.

"Proprioception" refers to a sense of position for a body. In the soft tissues around joints there are "sense of position receptors" which provide information to the brain which then in a reflex fashion instructs muscle to move to control position or movement. Although ligaments stabilise joints in a static sense, it is the dynamic stabilisation of joints achieved by muscles that cross them, that is primary in control. After an injury there is a proprioceptive lag which makes the ankle more susceptible to a lack of stabilisation because the muscle reflex is less responsive.

It has been found that many of the known body joint liners fail to achieve satisfactory results in that the healing process which involves the movement of tissue fluids can be too slow and the liner can be too uncomfortable to wear due to high skin pressures.

SUMMARY OF THE INVENTION

It is the object of the present invention to provide a body joint liner which will reduce such disadvantages or which will at least provide the public with a useful choice.

According to one aspect of the present invention there is provided a body joint liner having at least one divergent channel such that when in use on a persons body, tissue fluid flow is encouraged.

Preferably the channel is waist shaped.

Preferably the channel is centrally located.

Preferably the channel extends to a depressed area for a bone joint.

Preferably the liner has a first pressure gradient including a tapering thickness.

Preferably the liner has a second pressure gradient including a pattern of projections with a spacing pattern that increases along the liner.

Preferably the projections extend within the channel.

Preferably the liner is moulded from foam.

According to another aspect of the invention there is provided a body joint liner providing a first pressure gradient for tissue fluid flow when in use on a persons body.

Preferably the first pressure gradient comprises tapering liner thickness.

Preferably there is a channel.

Preferably the channel is waist shaped.

Preferably the channel is centrally located.

Preferably the channel extends to a depressed area for a bone joint.

Preferably the channel is a divergent channel.

Preferably the liner further includes a second pressure gradient such that when in use on a persons body tissue fluid flow is improved.

Preferably the second pressure gradient comprises a pattern of projections with a spacing pattern that increases along the length of the liner.

Preferably the projections extend within the channel.

Preferably the liner is moulded from foam.

According to another aspect of the invention there is provided a body joint liner providing a pressure gradient including a pattern of projections with a spacing that increases along the length of the liner.

Preferably the liner has a depressed area for a bone joint.

Preferably the liner has a divergent channel.

Preferably the liner is waist shaped.

Preferably the divergent channel is centrally located.

Preferably the projections extend within the length or the channel.

Preferably the liner has another gradient including a liner thickness which tapers or reduces in thickness.

Preferably the liner is moulded from foam.

To those skilled in the art to which the invention relates, many changes in construction and widely differing embodiments and applications of the invention will suggest themselves without departing from the scope of the invention as defined in the appended claims. The disclosures and the description herein are purely illustrative and are not intended to be in any sense limiting.

BRIEF DESCRIPTION OF THE DRAWINGS

An example of the invention is illustrated in the accompanying drawings in which:

FIG. 1 is a plan view of the body joint liner according to the invention.

FIG. 2 is a cross-section of the body joint liner along a line "AA" of FIG. 1.

FIG. 3 is a cross-section of the liner along line "BB" of FIG. 1.

DESCRIPTION OF THE PREFERRED EMBODIMENT

In FIG. 1 the body joint liner 1 shown is planar and waist shaped and elongate with a longitudinal center line A—A and ends 2 and 3, Also shown is a depressed area called the body joint area or ankle support area 4 and channel area 5 leading from the ankle support area 4 to end 2. Channel 5 provides an area which in use applies less pressure to the body of the user. The channel area 5 can be a divergent channel centrally located in the liner. Ankle support area 4 is a depressed area or region which in use fits over any bone joint or in this case the malleollar or projection on the distal end of the tibia or fibular as shown in FIGS. 2 and 3 of the drawing. The ankle support area 4 provides a line i.e. transverse line "CC" as shown in the figures, indicating the deepest point in the area and which centers on the ankle in use. As shown in FIGS. 2 and 3, the liner is generally convex in shape with a long length and a short length on either side of transverse line "CC". The long side forms a shallow valley shape (when compared to the depressed area on the opposite line side to the ankle support area 4.

Also shown in FIG. 1 are a series of different projections exhibiting different shapes and pattern configurations. A first projection pattern having projections 6, lies outside the central channel area 5 and may be regular in pattern. This pattern can be on an angle with respect to the longitudinal axis A—A or the transverse axis C—C of the liner as shown. Each projection 6 may comprise an elongate member. The first project pattern 6 is an exterior set of projections.

As shown in FIGS. 2 and 3 a first pressure gradient is shown. The first pressure gradient is provided by a tapering thickness 8 to the liner which creates a pressure gradient to encourage the flow of body fluids away from the ankle. The channel area has a border of projections which may include larger projections progressively down to smaller projections, as shown in FIG. 1. Thus the smaller projections may have a diameter of about 30% of the diameter of the larger projections.

A second pressure gradient as shown in FIG. 1, is defined as a pattern of second projections 7 with a spacing that increases along the length of the lines. The second projection pattern 7 is an interior set of projections.

The second projection pattern 7 lies in the ankle support area 4 which leads to the central channel area 5 extending to the far end 2. The second projection pattern 7 may not be regular in spacing and includes projections having a center spacing that increases from area 4 to the fat end 2. This means that the spacing of the projections becomes less dense. This increase in spacing or reduction of projection density further defines the second pressure gradient, to further encourage body fluid drainage. The projections are spread progressively so as to provide increasingly more channels for the fluid drainage. The projections can be called nipples or nubs or the like. In use the nipples will also absorb individual anatomy around the malleollar or the bone bumps on either side of the ankle. The grip on the individual ankle will therefore be improved. The nipples will exert a massaging effect as the wearer moves their ankle within the ankle brace. This will encourage greater movement of tissue fluids. The nipples will provide greater input to proprioceptive sensors in the soft tissue about the ankle and therefore enhance the stability imparted onto the ankle or subtalia joint by the surrounding muscles.

The liner may be constructed from moulded pressed foam and injection moulded materials or laminated materials or any combination thereof.

In use, the body joint liner is attached to the side of a body joint such as an ankle joint, after an injury.

Thus it can be seen from the foregoing that the present invention provides a body joint liner which when in use increases a persons tissue fluid flow and so improves the healing process.

What is claimed is:

1. A body joint liner for an ankle brace for human use, comprising:
   a planar surface elongate along a longitudinal centerline with first and second ends and a waist portion intermediate the first and second ends;
   a said planar surface having;
   a depressed body joint support area;
   a channel area leading from the depressed joint support area to the first end; and
   an interior set of projections located within the channel area and the depressed body joint support area said interior set of projections having a spacing pattern increasing along a length of the channel so that, in use on a person's body, body fluid flow is encouraged.

2. The liner of claim 1, further comprising:
   an exterior set of projections located outside the channel area, the individual projections of the exterior set of projections, in use, providing a pressure gradient on the person's body tissue to encourage the flow of body fluids away from the ankle.

3. The liner of claim 1, wherein the exterior set of projections is on an angle with respect to the longitudinal centerline.

4. The liner of claim 1, wherein the exterior set of projections is on an angle with respect to an axis transverse to the longitudinal centerline.

5. The liner of claim 1, wherein the interior set of projections at the depressed body joint support area pattern are regular in spacing and includes projections having a spacing increasing from the joint support area to the first end so that the interior set of projections become less dense moving from the joint support area to the first end.

6. The liner of claim 1, wherein, the channel area is a divergent channel centrally located along the centreline.

7. A body joint liner for a human ankle brace, comprising:
   a planar body having first and second ends elongate along a centerline and with a waist shaped region intermediate opposing first and second ends (3, 2);
   said planar body having depressed ankle support area (4) located nearer the first end and further from the second end, in use for supporting an ankle;
   an elongated channel area (5) leading from the ankle support area (4) to the second end, the channel area contoured to provide said depressed area which, in use, applies less pressure to the body of the user than remaining areas of the planar body,
   the elongate channel area and the ankle support area together having a border of projections which include larger projections at said first end and progressively smaller projections until said second end;
   a first pattern area of first projections (6) located in an entire region of the planar body outside the border of the elongate channel area and the ankle support area; and
   a second pattern area of second projections (7), located inside the border of and in the ankle support area and the elongate channel area, a spacing between the second projections increasing from the ankle support area (4) toward the second end (2) so that the density of the second projections decreases from the ankle support area (4) towards the second end (2).

8. The body joint liner of claim 7, wherein,
   the channel area is a divergent channel centrally located along the centerline of the planar body, and
   the ankle support area is located and sized so that, in use, the ankle support area fits over one of the malleollar and a projection on a distal end of the tibia or fibular, and
   in use, at a deepest point of the ankle support area, a transverse line can be drawn centering on the ankle.

9. The body joint liner of claim 8, wherein the channel area has a channel waist non-concurrently located with the waist of the planar body.

10. The body joint liner of claim 7, wherein the first projections are regular in pattern.

11. The body joint liner of claim 10, wherein the first projections are aligned on a non-orthogonal angle with respect to the centerline of the planar body, each first projection comprising an elongate member.

12. The body joint liner of claim 7, wherein the planar body has a tapering thickness (8) shaped to create a pressure gradient to encourage a flow of body fluids away from the ankle.

13. The body joint liner of claim 7, wherein the smaller border projections have a diameter of about 30% of a diameter of the larger border projections.

14. The body joint liner of claim 7, wherein the second projections are non-regular in spacing.

15. The body joint liner of claim 14, wherein the second projections are spread progressively toward the second end.

16. A body joint liner for a human ankle brace, comprising:

a planar body having first and second ends elongate along a centerline and with a waist shaped region located at a first point along the centerline intermediate opposing first and second ends (3, 2);

said planar body having a depressed ankle support area (4) located nearer the first end and further from the second end, in use for supporting an ankle;

a channel area (5) leading from the ankle support area (4) to the second end, the channel area contoured to provide said depressed area which, in use, applies less pressure to the body of the user than remaining areas of the planar body, the elongate channel area and the ankle support area together having a border of projections;

a first pattern area of first projections (6) located in an entire region of the planar body outside the border of the elongate channel area and the ankle support area; and a second pattern area of second projections (7), located inside the border of and in the ankle support area and the elongate channel area, so that, in use on a person's body, body fluid flow is encouraged, wherein, a spacing between the second projections increasing from the ankle support area (4) toward the second end (2) so that the density of the second projections decreases from the ankle support area (4) towards the second ends (2), and in use, at a deepest point of the ankle support area, a transverse line can be drawn centering on the ankle.

* * * * *